(12) United States Patent
Diolaiti et al.

(10) Patent No.: US 8,918,211 B2
(45) Date of Patent: Dec. 23, 2014

(54) MEDICAL ROBOTIC SYSTEM PROVIDING SENSORY FEEDBACK INDICATING A DIFFERENCE BETWEEN A COMMANDED STATE AND A PREFERRED POSE OF AN ARTICULATED INSTRUMENT

(75) Inventors: Nicola Diolaiti, Palo Alto, CA (US); Paul E. Lilagan, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 702 days.

(21) Appl. No.: 12/704,669

(22) Filed: Feb. 12, 2010

(65) Prior Publication Data

US 2011/0202068 A1    Aug. 18, 2011

(51) Int. Cl.
*A61B 19/00* (2006.01)
*G05B 19/04* (2006.01)
*G05B 19/18* (2006.01)

(52) U.S. Cl.
CPC ......... *A61B 19/2203* (2013.01); *A61B 19/5212* (2013.01); *A61B 2019/502* (2013.01); *A61B 2019/2296* (2013.01); *A61B 2019/2223* (2013.01); *A61B 2019/2292* (2013.01); *A61B 2019/5206* (2013.01); *A61B 2019/2234* (2013.01); *Y10S 901/33* (2013.01); *Y10S 901/34* (2013.01)
USPC ........... 700/257; 700/252; 700/254; 606/130; 901/33; 901/34

(58) Field of Classification Search
CPC ........... A61B 19/2203; A61B 19/5212; A61B 2019/2223; A61B 2019/5206; A61B 2019/2292; A61B 2019/2296; A61B 2019/502; A61B 2019/2234
USPC ........ 606/1, 130; 700/245–265; 901/2–45, 50
See application file for complete search history.

(56) References Cited

U.S. PATENT DOCUMENTS

| 4,644,237 A | 2/1987 | Frushour et al. |
| 4,791,934 A | 12/1988 | Brunnett |
| 4,831,549 A | 5/1989 | Red et al. |
| 4,837,703 A | 6/1989 | Kakazu et al. |
| 4,979,949 A | 12/1990 | Matsen, III et al. |

(Continued)

FOREIGN PATENT DOCUMENTS

| EP | 812662 A1 | 12/1997 |
| EP | 1125557 A2 | 8/2001 |

(Continued)

OTHER PUBLICATIONS

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

(Continued)

*Primary Examiner* — Khoi Tran
*Assistant Examiner* — Abby Lin

(57) ABSTRACT

A medical robotic system includes an entry guide with articulated instruments extending out of its distal end. A controller is configured to command manipulation of one of the articulated instruments towards a state commanded by operator manipulation of an input device while commanding sensory feedback to the operator indicating a difference between the commanded state and a preferred pose of the articulated instrument, so that the sensory feedback serves to encourage the operator to return the articulated instrument back to its preferred pose.

60 Claims, 10 Drawing Sheets

(56) References Cited

U.S. PATENT DOCUMENTS

| | | | |
|---|---|---|---|
| 5,086,401 A | 2/1992 | Glassman et al. | |
| 5,230,338 A | 7/1993 | Allen et al. | |
| 5,343,385 A | 8/1994 | Joskowicz et al. | |
| 5,408,409 A | 4/1995 | Glassman et al. | |
| 5,417,210 A | 5/1995 | Funda et al. | |
| 5,528,955 A | 6/1996 | Hannaford et al. | |
| 5,704,897 A | 1/1998 | Truppe | |
| 5,748,767 A | 5/1998 | Raab | |
| 5,749,362 A * | 5/1998 | Funda et al. | 600/407 |
| 5,755,725 A | 5/1998 | Druais | |
| 5,820,545 A | 10/1998 | Arbter et al. | |
| 5,820,623 A | 10/1998 | Ng | |
| 5,831,408 A | 11/1998 | Jacobus et al. | |
| 5,835,693 A | 11/1998 | Lynch et al. | |
| 5,876,325 A | 3/1999 | Mizuno et al. | |
| 5,950,629 A | 9/1999 | Taylor et al. | |
| 5,987,591 A | 11/1999 | Jyumonji | |
| 6,115,053 A | 9/2000 | Perlin | |
| 6,120,433 A | 9/2000 | Mizuno et al. | |
| 6,184,868 B1 | 2/2001 | Shahoian et al. | |
| 6,204,620 B1 * | 3/2001 | McGee et al. | 318/568.11 |
| 6,224,542 B1 | 5/2001 | Chang et al. | |
| 6,325,808 B1 | 12/2001 | Bernard et al. | |
| 6,342,889 B1 | 1/2002 | Callahan | |
| 6,371,909 B1 | 4/2002 | Hoeg et al. | |
| 6,398,726 B1 | 6/2002 | Ramans et al. | |
| 6,424,885 B1 * | 7/2002 | Niemeyer et al. | 700/245 |
| 6,442,417 B1 | 8/2002 | Shahidi et al. | |
| 6,456,901 B1 | 9/2002 | Xi et al. | |
| 6,459,926 B1 | 10/2002 | Nowlin et al. | |
| 6,468,265 B1 | 10/2002 | Evans et al. | |
| 6,493,608 B1 | 12/2002 | Niemeyer | |
| 6,522,906 B1 | 2/2003 | Salisbury, Jr. et al. | |
| 6,574,355 B2 | 6/2003 | Green | |
| 6,643,563 B2 | 11/2003 | Hosek et al. | |
| 6,645,196 B1 | 11/2003 | Nixon et al. | |
| 6,659,939 B2 | 12/2003 | Moll et al. | |
| 6,770,081 B1 | 8/2004 | Cooper et al. | |
| 6,837,883 B2 | 1/2005 | Moll et al. | |
| 6,847,922 B1 | 1/2005 | Wampler, II | |
| 6,926,709 B2 | 8/2005 | Bieger et al. | |
| 6,991,627 B2 | 1/2006 | Madhani et al. | |
| 7,041,053 B2 | 5/2006 | Miyake | |
| 7,155,315 B2 | 12/2006 | Niemeyer et al. | |
| 7,181,315 B2 | 2/2007 | Watanabe et al. | |
| 7,194,118 B1 | 3/2007 | Harris et al. | |
| 7,491,198 B2 | 2/2009 | Kockro | |
| 7,725,214 B2 | 5/2010 | Diolaiti | |
| 7,806,891 B2 | 10/2010 | Nowlin et al. | |
| 7,819,859 B2 | 10/2010 | Prisco et al. | |
| 7,963,913 B2 | 6/2011 | Devengenzo et al. | |
| 7,979,157 B2 | 7/2011 | Anvari | |
| 7,996,110 B2 | 8/2011 | Lipow et al. | |
| 8,062,288 B2 | 11/2011 | Cooper et al. | |
| 8,120,301 B2 | 2/2012 | Goldberg et al. | |
| 8,130,907 B2 | 3/2012 | Maurer, Jr. et al. | |
| 8,155,479 B2 | 4/2012 | Hoffman et al. | |
| 8,170,716 B2 | 5/2012 | Coste-Maniere et al. | |
| 8,256,319 B2 | 9/2012 | Cooper et al. | |
| 8,315,720 B2 | 11/2012 | Mohr et al. | |
| 8,335,590 B2 | 12/2012 | Costa et al. | |
| 8,620,473 B2 | 12/2013 | Diolaiti et al. | |
| 2001/0035871 A1 | 11/2001 | Bieger et al. | |
| 2002/0045905 A1 | 4/2002 | Gerbi et al. | |
| 2002/0120188 A1 | 8/2002 | Brock et al. | |
| 2003/0032878 A1 | 2/2003 | Shahidi | |
| 2003/0055410 A1 | 3/2003 | Evans et al. | |
| 2003/0109780 A1 | 6/2003 | Coste-Maniere et al. | |
| 2003/0114730 A1 | 6/2003 | Hale et al. | |
| 2003/0167103 A1 | 9/2003 | Tang et al. | |
| 2003/0225479 A1 | 12/2003 | Waled | |
| 2004/0077940 A1 * | 4/2004 | Kienzle et al. | 600/424 |
| 2004/0106916 A1 | 6/2004 | Quaid et al. | |
| 2004/0238732 A1 | 12/2004 | State et al. | |
| 2004/0249508 A1 | 12/2004 | Suita et al. | |
| 2004/0254679 A1 | 12/2004 | Nagasaka | |
| 2005/0022158 A1 | 1/2005 | Launay et al. | |
| 2005/0054895 A1 | 3/2005 | Hoeg et al. | |
| 2005/0059960 A1 | 3/2005 | Simaan et al. | |
| 2005/0096502 A1 | 5/2005 | Khalili | |
| 2005/0203380 A1 | 9/2005 | Sauer et al. | |
| 2005/0228365 A1 * | 10/2005 | Wang et al. | 606/1 |
| 2005/0251113 A1 | 11/2005 | Kienzle, III | |
| 2006/0142657 A1 * | 6/2006 | Quaid et al. | 600/424 |
| 2006/0258938 A1 | 11/2006 | Hoffman et al. | |
| 2006/0261770 A1 | 11/2006 | Kishi et al. | |
| 2007/0013336 A1 | 1/2007 | Nowlin et al. | |
| 2007/0032906 A1 | 2/2007 | Sutherland et al. | |
| 2007/0038080 A1 | 2/2007 | Salisbury, Jr. et al. | |
| 2007/0135803 A1 | 6/2007 | Belson | |
| 2007/0142968 A1 | 6/2007 | Prisco et al. | |
| 2007/0255454 A1 | 11/2007 | Dariush | |
| 2007/0265491 A1 | 11/2007 | Krag et al. | |
| 2007/0270650 A1 | 11/2007 | Eno et al. | |
| 2007/0283970 A1 | 12/2007 | Mohr et al. | |
| 2007/0287884 A1 | 12/2007 | Schena | |
| 2007/0287992 A1 | 12/2007 | Diolaiti et al. | |
| 2008/0004603 A1 | 1/2008 | Larkin et al. | |
| 2008/0033240 A1 | 2/2008 | Hoffman et al. | |
| 2008/0065105 A1 | 3/2008 | Larkin et al. | |
| 2008/0065109 A1 | 3/2008 | Larkin | |
| 2008/0071291 A1 | 3/2008 | Duval et al. | |
| 2008/0081992 A1 | 4/2008 | Kagermeier | |
| 2008/0118115 A1 | 5/2008 | Williamson | |
| 2008/0140087 A1 | 6/2008 | Barbagli | |
| 2008/0161830 A1 | 7/2008 | Sutherland et al. | |
| 2008/0188986 A1 | 8/2008 | Hoppe | |
| 2008/0243142 A1 | 10/2008 | Gildenberg | |
| 2008/0247506 A1 | 10/2008 | Maschke | |
| 2008/0287963 A1 | 11/2008 | Rogers et al. | |
| 2009/0012531 A1 | 1/2009 | Quaid et al. | |
| 2009/0024142 A1 | 1/2009 | Ruiz Morales | |
| 2009/0036902 A1 * | 2/2009 | DiMaio et al. | 606/130 |
| 2009/0088634 A1 | 4/2009 | Zhao et al. | |
| 2009/0192524 A1 | 7/2009 | Itkowitz et al. | |
| 2009/0228145 A1 | 9/2009 | Hodgson et al. | |
| 2009/0248036 A1 | 10/2009 | Hoffman et al. | |
| 2009/0326318 A1 | 12/2009 | Tognaccini et al. | |
| 2009/0326552 A1 * | 12/2009 | Diolaiti | 606/130 |
| 2009/0326553 A1 * | 12/2009 | Mustufa et al. | 606/130 |
| 2009/0326556 A1 * | 12/2009 | Diolaiti et al. | 606/130 |
| 2009/0326711 A1 | 12/2009 | Chang et al. | |
| 2010/0106356 A1 * | 4/2010 | Trepagnier et al. | 701/25 |
| 2010/0198232 A1 | 8/2010 | Diolaiti | |
| 2010/0249657 A1 * | 9/2010 | Nycz et al. | 600/587 |
| 2010/0274087 A1 | 10/2010 | Diolaiti et al. | |
| 2011/0040305 A1 | 2/2011 | Gomez et al. | |
| 2011/0040404 A1 | 2/2011 | Diolaiti et al. | |
| 2011/0071675 A1 | 3/2011 | Wells et al. | |
| 2011/0196199 A1 | 8/2011 | Donhowe et al. | |
| 2012/0059391 A1 | 3/2012 | Diolaiti et al. | |
| 2012/0059392 A1 | 3/2012 | Diolaiti | |
| 2013/0231680 A1 | 9/2013 | Diolaiti et al. | |
| 2014/0055489 A1 | 2/2014 | Itkowitz et al. | |
| 2014/0222021 A1 | 8/2014 | Diolaiti et al. | |

FOREIGN PATENT DOCUMENTS

| | | |
|---|---|---|
| JP | H08154321 A | 6/1996 |
| JP | H11000309 A | 6/1999 |
| JP | 2007029232 A | 2/2007 |
| JP | 2009006410 A | 1/2009 |
| JP | 2009012106 A | 1/2009 |
| WO | WO-2004014244 | 2/2004 |
| WO | WO-2006079108 A1 | 7/2006 |
| WO | WO-2007030173 A1 | 3/2007 |
| WO | WO-2007047782 A2 | 4/2007 |
| WO | WO-2007088208 A1 | 8/2007 |
| WO | WO-2007136768 A2 | 11/2007 |
| WO | WO-2007146987 A2 | 12/2007 |
| WO | WO-200802830 A2 | 1/2008 |
| WO | WO-2008103383 A1 | 8/2008 |
| WO | WO-2009034477 | 3/2009 |

(56) References Cited

FOREIGN PATENT DOCUMENTS

| WO | WO-2009037576 | 3/2009 |
|---|---|---|
| WO | WO-2009158164 A1 | 12/2009 |
| WO | WO-2010039394 A1 | 4/2010 |

OTHER PUBLICATIONS

Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 171-1176, vol. 2.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

International Search Report and Written Opinion for Application No. PCT/US2012/064379, mailed on Mar. 29, 2013, 12 pages.

International Search Report and Written Opinion for Application No. PCT/US2012/064400, mailed on Mar. 27, 2013, 10 pages.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

PCT/US07/71850 International Search Report and Written Opinion of the International Searching Authority, mailed Feb. 13, 2009, 9 pages.

PCT/US09/46234 International Search Report and Written Opinion of the International Searching Authority, mailed Sep. 9, 2009, 13 pages.

PCT/US09/56078 International Search Report and Written Opinion of the International Searching Authority, mailed Jan. 20, 2010, 12 pages.

PCT/US10/28886 International Search Report and Written Opinion of the International Searching Authority, mailed Jul. 6, 2010, 11 pages.

PCT/US10/28897 International Search Report and Written Opinion of the International Searching Authority, mailed Jul. 19, 2010, 16 pages.

PCT/US10/38246 International Search Report and Written Opinion of the International Searching Authority, mailed Sep. 14, 2010, 17 pages.

PCT/US2011/036109 International Search Report and Written Opinion of the International Searching Authority, mailed Oct. 19, 2011, 16 pages.

PCT/US2011/036109 Invitation to Pay Additional Fees and Partial International Search Report, mailed Aug. 18, 2011, 5 pages.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

\* cited by examiner

MEDICAL ROBOTIC SYSTEM PROVIDING SENSORY FEEDBACK INDICATING A DIFFERENCE BETWEEN A COMMANDED STATE AND A PREFERRED POSE OF AN ARTICULATED INSTRUMENT

FIELD OF THE INVENTION

The present invention generally relates to medical robotic systems and in particular, to a medical robotic system providing sensory feedback indicating a difference between a commanded state and a preferred pose of an articulated instrument.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Articulated instruments such as an articulated camera and a plurality of articulated surgical tools, which are used to perform the medical procedure, may then be inserted into a proximal end of the entry guide so as to extend out of its distal end. Thus, the entry guide accommodates a single entry aperture for multiple instruments while keeping the instruments bundled together as it guides them toward the work site.

A number of challenges arise in medical robotic systems using such a bundled unit, however, because of the close proximity of the articulated camera and tool instruments. For example, because the camera instrument has proximal articulations (e.g., joints) that are not visible from the distal tip camera view, the surgeon can lose track of the current state of such articulations when moving the camera and consequently, their available range of motion. Also, when the articulations of the camera and tool instruments are out of view of the camera and therefore, not visible to the surgeon through its captured images, the surgeon may inadvertently drive links of the tools and/or camera instruments to crash into one another while telerobotically moving the articulated instruments to perform a medical procedure. In either case, the safety of the patient may be jeopardized and the successful and/or timely completion of the medical procedure may be adversely impacted.

OBJECTS AND SUMMARY OF THE INVENTION

Accordingly, one object of one or more aspects of the present invention is a medical robotic system, and method implemented therein, that provides an operator a means for selecting a preferred pose for an articulated instrument, which serves as a biasing point for operator commanded movement of the articulated instrument.

Another object of one or more aspects of the present invention is a medical robotic system, and method implemented therein, that provides a sensory cue to an operator as the operator commands an articulated instrument to be moved from its preferred pose.

Another object of one or more aspects of the present invention is a medical robotic system, and method implemented therein, that provides a haptic force to an operator that nudges the operator to move an articulated instrument back to its preferred pose.

These and additional objects are accomplished by the various aspects of the present invention, wherein briefly stated, one aspect is a medical robotic system comprising: an entry guide; a plurality of articulated instruments extending through the entry guide; an input device associated with one of the plurality of articulated instruments; and a controller configured to command manipulation of the associated articulated instrument towards a state commanded by operator manipulation of the input device while commanding sensory feedback to the operator indicating a difference between the operator commanded state and a preferred pose of the associated articulated instrument.

Another aspect is a medical robotic system comprising: an entry guide; a plurality of articulated instruments extending through the entry guide; an input device associated with the entry guide; and a controller configured to command manipulation of the entry guide towards a state commanded by operator manipulation of the input device while commanding sensory feedback to the operator indicating a difference between the operator commanded state and a preferred pose of the entry guide.

Another aspect is a method implemented in a medical robotic system having an entry guide, a plurality of articulated instruments extending through the entry guide, and an input device associated with one of the plurality of articulated instruments, the method comprising: manipulating the associated articulated instrument towards a state commanded by operator manipulation of the input device; and providing sensory feedback to the operator indicating a difference between the operator commanded state and a preferred pose of the associated articulated instrument.

Another aspect is a method implemented in a medical robotic system having an entry guide, a plurality of articulated instruments extending through the entry guide, and an input device associated with the entry guide, the method comprising: manipulating the entry guide towards a state commanded by operator manipulation of the input device; and providing sensory feedback to the operator indicating a difference between the operator commanded state and a preferred pose of the entry guide.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
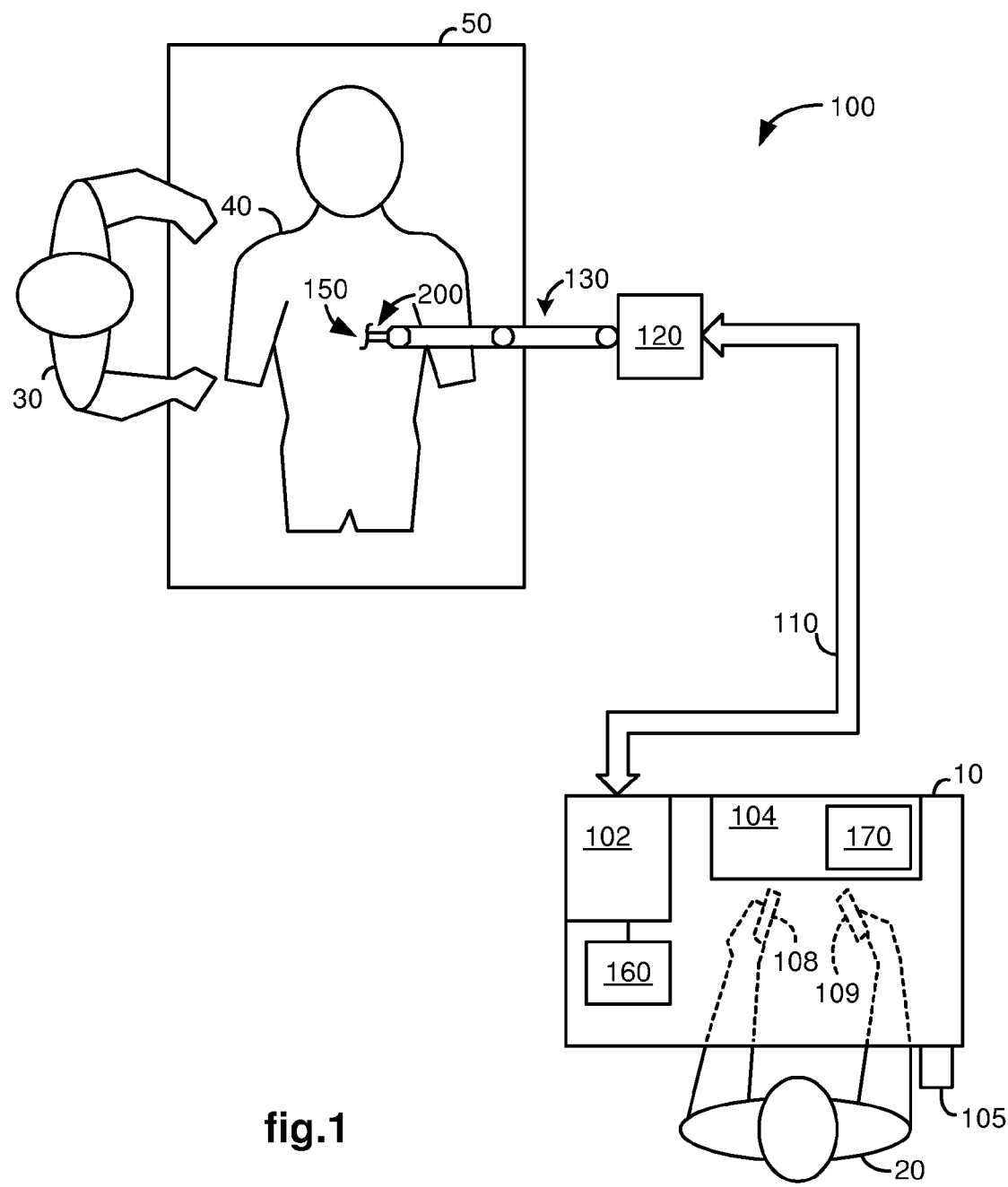
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw relative to a longitudinal axis of the entry guide 200 about a pivot point (also referred to as a remote center "RC") which is located at the entry aperture 150.

The console 10 includes a three-dimensional (3-D) monitor 104 for displaying a 3-D image of a surgical site to the Surgeon, left and right hand-manipulatable input devices 108, 109, a foot pedal 105, and a processor 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160, a Graphical User Interface (GUI) 170, and convention computer inputs such as a keyboard and computer mouse.

The console 10 is usually located in the same room as the Patient so that the Surgeon may directly monitor the procedure, is physically available if necessary, and is able to speak to the Assistant(s) directly rather than over the telephone or other communication medium. However, the Surgeon can also be located in a different room, a completely different building, or other remote location from the Patient allowing for remote surgical procedures.

Figure 3:
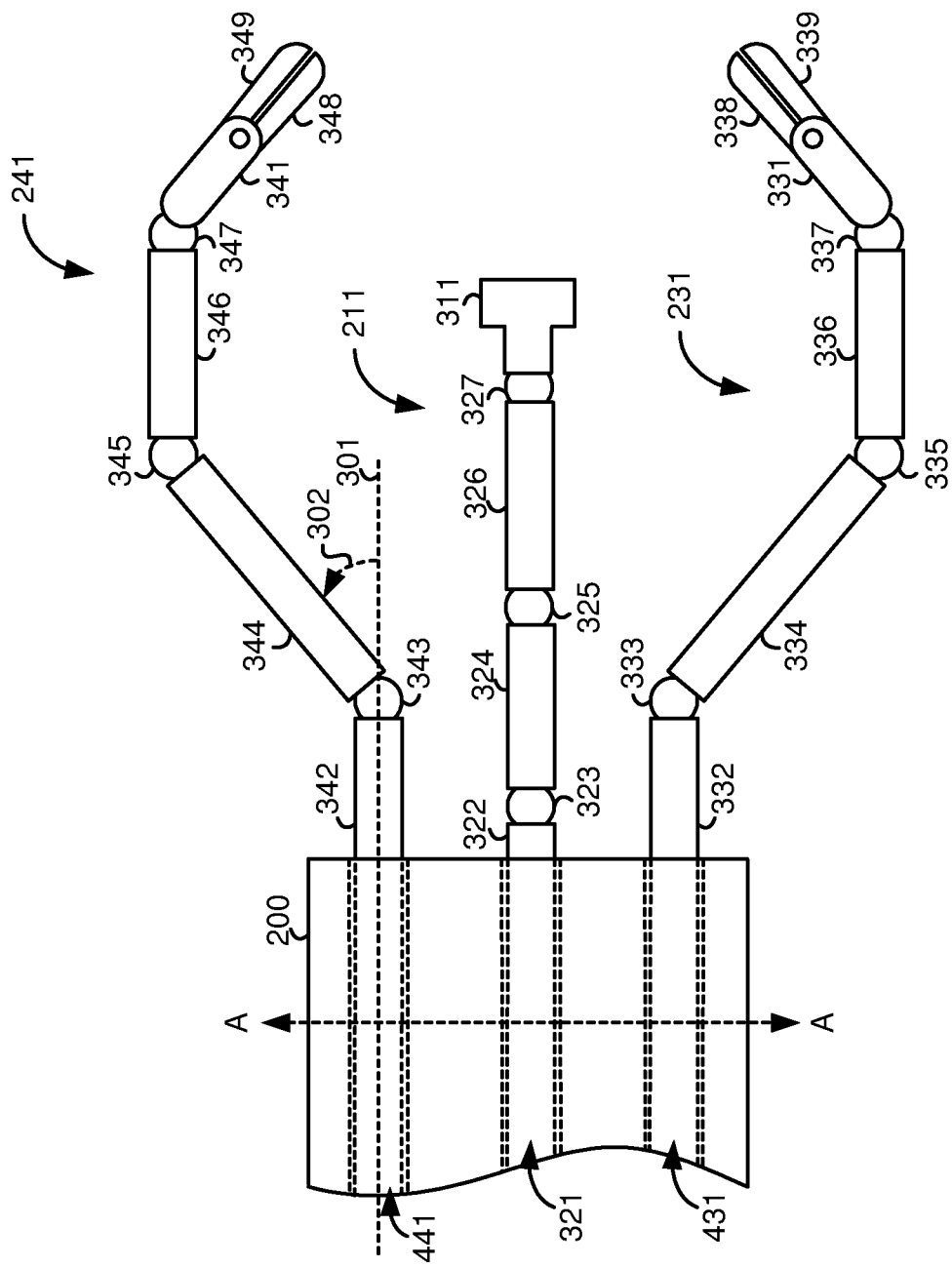
FIGS. 3-4 respectively illustrate top and right side views of articulated instruments extending out of a distal end of an entry guide in a medical robotic system utilizing aspects of the present invention.
Figure 4:
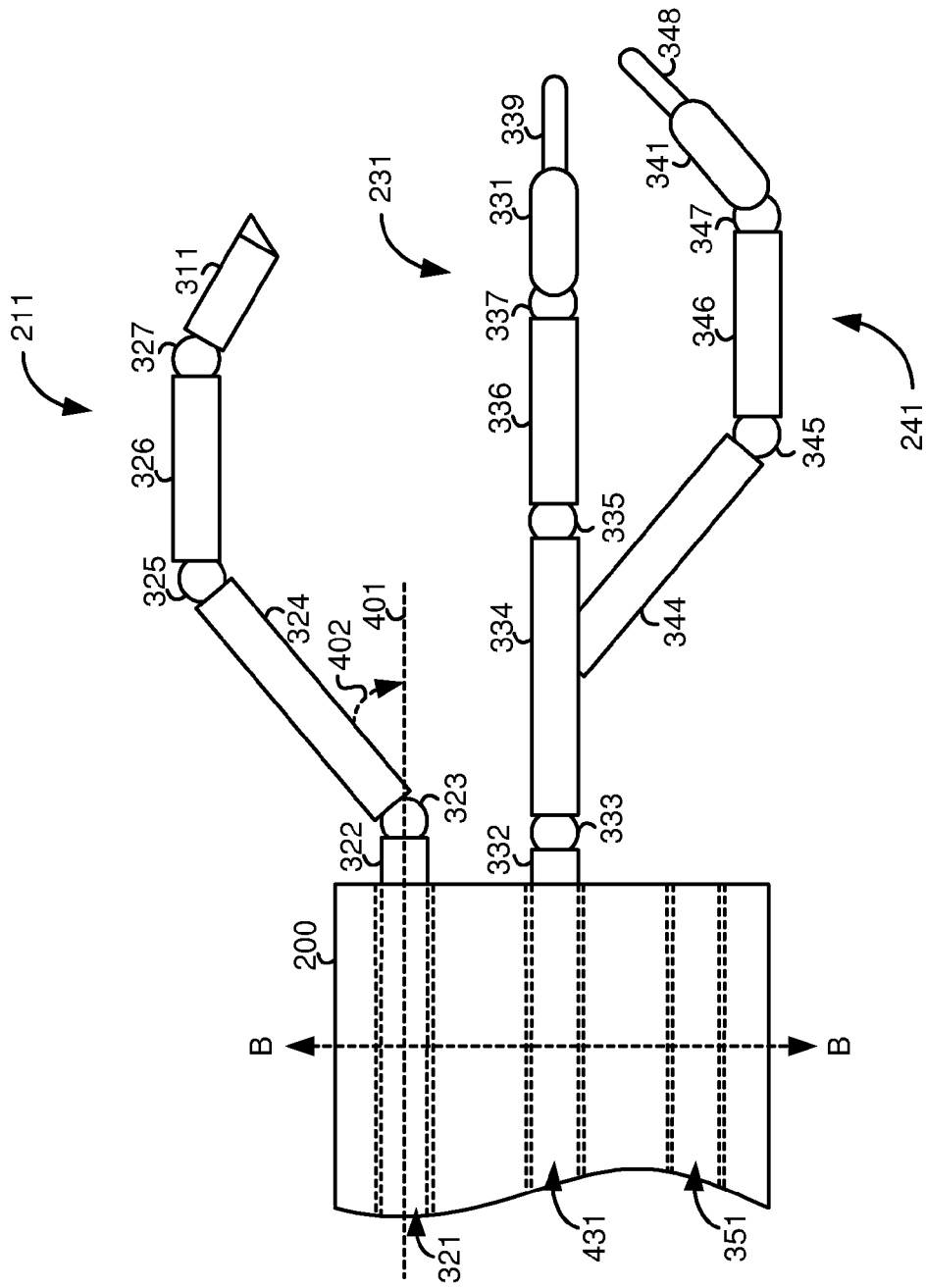
Figure 5:
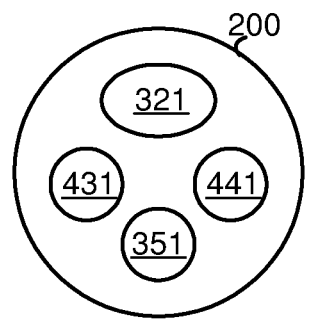
FIG. 5 illustrates a distal end view of an entry guide with passages defined therein as used in a medical robotic system utilizing aspects of the present invention.

As shown in FIGS. 3-4, the entry guide 200 has articulated instruments such as surgical tools 231, 241 and a stereo camera 211 extending out of its distal end. Although only two tools 231, 241 are shown, the entry guide 200 may guide additional instruments as required for performing a medical procedure at a work site in the Patient. For example, as shown in the entry guide 200 side and distal end views of FIGS. 4 and 5, passage 351 is available for extending another articulated instrument through the entry guide 200 and out through its distal end. Each of the surgical tools 231, 241 is associated with one of the input devices 108, 109 in a tool following mode. The Surgeon performs a medical procedure by manipulating the input devices 108, 109 so that the processor 102 causes corresponding movement of their respectively associated surgical tools 231, 241 while the Surgeon views the work site in 3-D on the console monitor 104 as images of the work site are being captured by the camera 211.

In this example, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 may transform the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to implement the various controllers described herein to translate and transfer the mechanical motion of input devices 108, 109 through control signals over bus 110 so that the Surgeon can effectively manipulate and otherwise move devices, such as the tools 231, 241, camera 211, and entry guide 200, that are selectively associated with the input devices 108, 109 at the time.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of general aspects of a medical robotic system such as described herein, see, e.g., U.S. Pat. No. 6,493,608 "Aspects of a Control System of a Minimally Invasive Surgical Apparatus," U.S. Pat. No. 6,671,581 "Camera Referenced Control in a Minimally Invasive Surgical Apparatus," and U.S. Pat. Application Pub. No. U.S. 2008/007129 "Minimally Invasive Surgical System," which are incorporated herein by reference.

Figure 2:
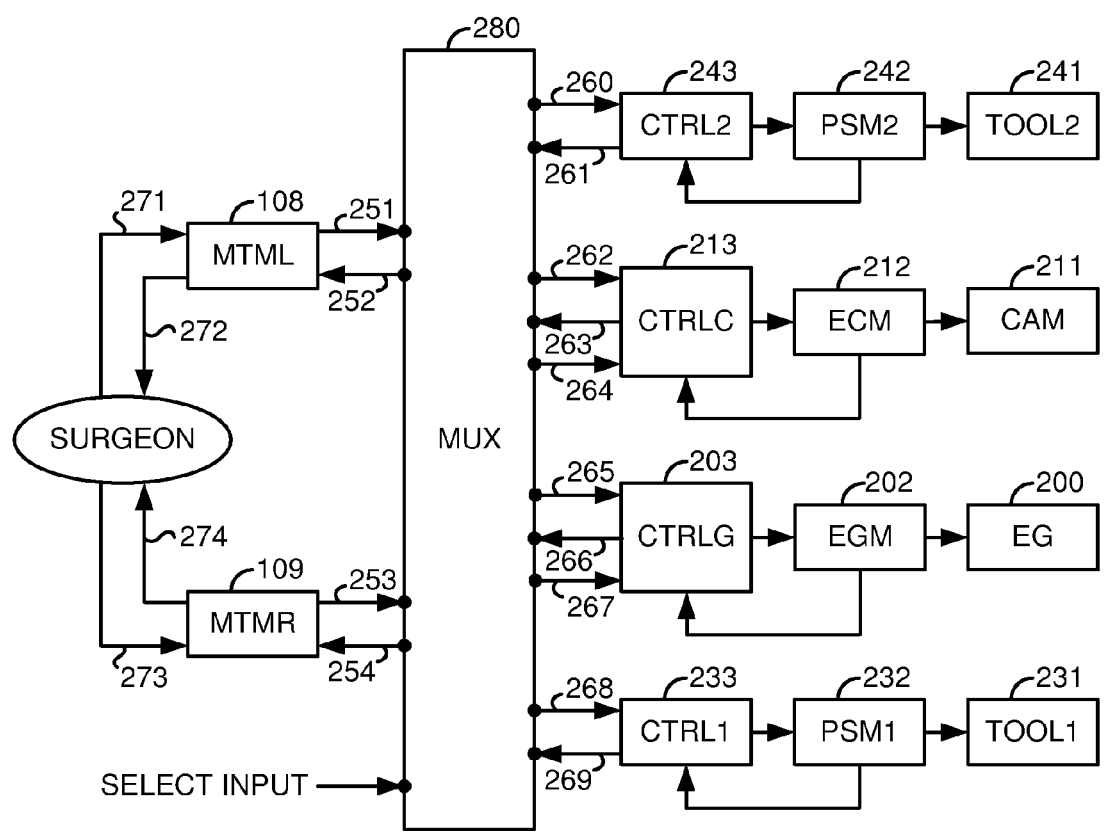
FIG. 2 illustrates a block diagram of components for controlling and selectively associating device manipulators to left and right hand-manipulatable input devices in a medical robotic system utilizing aspects of the present invention.

FIG. 2 illustrates, as an example, a block diagram of components for controlling and selectively associating device manipulators (and their respective devices) to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The tools 231, 241 and camera 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGM) 202.

Each of the instrument manipulators 232, 242, 212 is a mechanical assembly that carries actuators and provides a mechanical, sterile interface to transmit motion to its respective articulated instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a predetermined fashion. Each set of mechanically constrained joints implements a specific axis of motion, and constraints may be devised to pair rotational joints (e.g., joggle joints). Note also that in this way the instrument may have more joints than the available actuators.

Since the controllers 233, 243, 213 are generally implemented as computer code in the processor 102, they are each programmed to be reconfigurable by an operator of the system 100 to control either a tool or a camera instrument. Thus, if a tool instrument is physically switched for a camera instrument or vice versa in the system, its controller may be reconfigured to accommodate the newly installed device.

In this example, each of the input devices 108, 109 may be selectively associated with one of the devices 211, 231, 241, 200 so that the associated device may be controlled by the input device through its controller and manipulator. The operator may perform such selection in a conventional manner by interacting with a menu on the GUI 170 or providing voice commands recognized by the voice recognition system 160 or by inputting such associations into the system 100 using an input device such as a touchpad (not shown) or interacting with special purpose buttons provided on the input devices 108, 109 or foot pedal 105. In each such implementation, a select input is generated and provided to a multiplexer (MUX) 280, which is also generally implemented in the processor 102. Depending upon the value (i.e., the combination of 1's and 0's) provided by the select input, different combinations of cross-switching are selectable.

For example, a first value for the select input to the MUX 280 places the left and right input devices 108, 109 in "tool following modes" wherein they are respectively associated with the first and second surgical tools 241, 231, which are telerobotically controlled through their respective controllers 243, 233 and manipulators 242, 232 so that the Surgeon may perform a medical procedure on the Patient while the entry guide 200 is locked in place. In this configuration, the MUX 280 cross-switches to respectively connect output and input 251, 252 of the input device 108 to input and output 260, 261 of the tool controller 243; and respectively connect output and input 253, 254 of the input device 109 to input and output 268, 269 of the tool controller 233.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller.

For example, a second value for the select input to the MUX 280 places the left and right input devices 108, 109 in a "two-handed, camera positioning mode" wherein they are associated with the camera 211, which is telerobotically controlled through its controller 213 and manipulator 212 so that the Surgeon may position the camera 211 while the surgical tools 231, 241 and entry guide 200 are locked in place by their respective controllers 233, 243, 203. In this case, the input devices 108, 109 may be used in tandem to control the camera instrument 211, such as using a virtual handlebar image referenced control technique in which a point midway between pivot points of the input devices 108, 109 is used to control movement of the camera instrument 211. In this configuration, the MUX 280 cross-switches to respectively connect output and input 251, 252 of the input device 108 to input and output 262, 263 of the camera controller 213; and respectively connect output and input 253, 254 of the input device 109 to input and output 264, 263 of the camera controller 213.

On the other hand, a third value for the select input to the MUX 280 places the left and right input devices 108, 109 in an "two-handed, entry guide positioning mode" wherein they are associated with the entry guide 200, which is telerobotically controlled through its controller 203 and manipulator 202 so that the Surgeon may position the entry guide 200 while the surgical tools 231, 241 and camera 211 are locked in place relative to the entry guide 200 by their respective controllers 233, 243, 213. In this configuration, the MUX 280 cross-switches to respectively connect output and input 251, 252 of the input device 108 to input and output 262, 263 of the camera controller 213; and respectively connect output and input 253, 254 of the input device 109 to input and output 264, 263 of the camera controller 213.

If only one of the input devices 108, 109 is to be used for positioning the camera 211 or the entry guide 200, then another value for the select input to the MUX 280 may be provided by the operator to place the selected input device in a "single-handed, camera or entry guide positioning mode" so that the selected input device is associated with the camera or entry guide, as the case may be, which is telerobotically controlled through its controller and manipulator so that the Surgeon may position the device. Meanwhile, the other input device may either be "soft locked" in position by its controller until the camera or entry guide positioning is completed or the other input device may still be available to the Surgeon to control its associated surgical tool during camera or entry guide repositioning. For example, when the input device 108 is in "single-handed, camera positioning mode," the MUX 280 cross-switches to respectively connect output and input 251, 252 of the input device 108 to input and output 262, 263 of the camera controller 213. In this case, no connection is made to the second input 264 of the camera controller 213.

FIGS. 3-4 respectively illustrate, as examples, top and right side views of a distal end of the entry guide 200 with the camera 211 and surgical tools 231, 241 extending outward. The articulated camera 211 extends through passage 321 and the articulated surgical tools 231, 241 respectively extend through passages 431, 441 of the entry guide 200. The camera 211 includes a tip 311, first, second, and third links 322, 324, 326, first and second joint assemblies (also referred to herein simply as "joints") 323, 325, and a wrist assembly 327. The tip 311 houses a stereo camera connected to a camera controller and a fiber-optic cable connected to an external light source. The first joint assembly 323 couples the first and second links 322, 324 and the second joint assembly 325 couples the second and third links 324, 326 so that the second link 324 may pivot about the first joint assembly 323 in pitch and yaw while the first and third links 322, 326 remain parallel to each other.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal axis in roll as well as move in and out (e.g., insertion towards the work site and retraction from the worksite) through the passage 321. The wrist assembly 327 also has pitch and yaw angular movement capability so that the camera's tip 311 may be oriented up or down and to the right or left, and combinations thereof.

The joints and links of the tools 231, 241 are similar in construction and operation to those of the camera 211. In particular, the tool 231 includes an end effector 331 (having jaws 338, 339), first, second, and third links 332, 334, 336, first and second joint assemblies 333, 335, and a wrist assembly 337 that are driven by actuators such as described in reference to FIG. 6 (plus an additional actuator for actuating the end effector 331). Likewise, the tool 241 includes an end effector 341 (having jaws 348, 349), first, second, and third links 342, 344, 346, first and second joint assemblies 343, 345, and a wrist assembly 347 that are also driven by actuators such as described in reference to FIG. 6 (plus an additional actuator for actuating the end effector 341).

Figure 6:
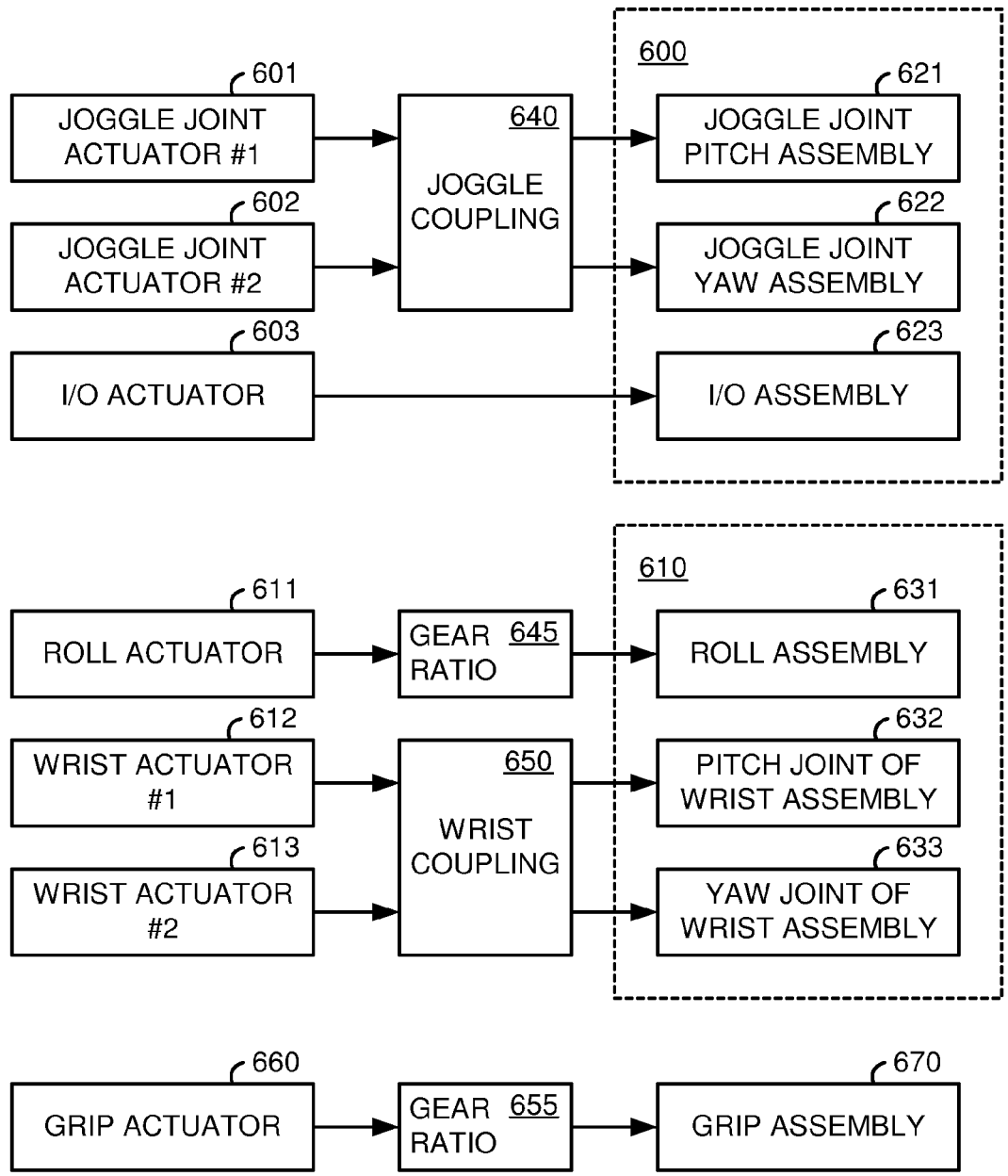
FIG. 6 illustrates a block diagram of interacting components of an articulated instrument manipulator and an articulated instrument as used in a medical robotic system utilizing aspects of the present invention.

FIG. 6 illustrates, as an example, a diagram of interacting parts of an articulated instrument (such as the articulated camera 211 and the articulated surgical tools 231, 241) and its corresponding instrument manipulator (such as the camera manipulator 212 and the tool manipulators 232, 242). Each of the instruments includes a number of actuatable assemblies 621-623, 631-633, 670 for effectuating movement of the instrument (including its end effector), and its corresponding manipulator includes a number of actuators 601-603, 611-613, 660 for actuating the actuatable assemblies.

In addition, a number of interface mechanisms may also be provided. For example, pitch/yaw coupling mechanisms 640, 650 (respectively for the joggle joint pitch/yaw and the wrist pitch/yaw) and gear ratios 645, 655 (respectively for the instrument roll and the end effector actuation) are provided in a sterile manipulator/instrument interface to achieve the required range of motion of the instrument joints in instrument joint space while both satisfying compactness constraints in the manipulator actuator space and preserving accurate transmissions of motion across the interface. Although shown as a single block 640, the coupling between the joggle joint actuators 601, 602 (differentiated as #1 and #2) and joggle joint pitch/yaw assemblies 621, 622 may include a pair of coupling mechanisms—one on each side of the sterile interface (i.e., one on the manipulator side of the interface and one on the instrument side of the interface). Likewise, although shown as a single block 650, the coupling between the wrist actuators 612, 613 (differentiated as #1 and #2) and wrist pitch/yaw joint assemblies 632, 633 may also comprise a pair of coupling mechanisms—one on each side of the sterile interface.

Both the joggle joint pitch assembly 621 and the joggle joint yaw assembly 622 share the first, second and third links (e.g., links 322, 324, 326 of the articulated camera 211) and the first and second joints (e.g., joints 322, 325 of the articulated camera 211). In addition to these shared components, the joggle joint pitch and yaw assemblies 621, 622 also include mechanical couplings that couple the first and second joints (through joggle coupling 640) to the joggle joint pitch and yaw actuators 601, 602 so that the second link may controllably pivot about a line passing through the first joint and along an axis that is latitudinal to the longitudinal axis of the first link (e.g., link 322 of the articulated camera 211) and the second link may controllably pivot about a line passing through the first joint and along an axis that is orthogonal to both the latitudinal and longitudinal axes of the first link.

The in/out (I/O) assembly 623 includes the first link (e.g., link 322 of the articulated camera 211) and interfaces through a drive train coupling the in/out (I/O) actuator 603 to the first link so that the first link is controllably moved linearly along its longitudinal axis 401 by actuation of the I/O actuator 603. The roll assembly 631 includes the first link and interfaces through one or more gears (i.e., having the gear ratio 645) that couple a rotating element of the roll actuator 611 (such as a rotor of a motor) to the first link so that the first link is controllably rotated about its longitudinal axis by actuation of the roll actuator 611.

The instrument manipulator (e.g., camera manipulator 212) includes wrist actuators 612, 613 that actuate through wrist coupling 650 pitch and yaw joints 632, 633 of the wrist assembly (e.g., wrist assembly 327 of the articulated camera 211) so as to cause the instrument tip (e.g., camera tip 311) to controllably pivot in an up-down (i.e., pitch) and side-to-side (i.e., yaw) directions relative to the wrist assembly. The grip assembly 670 includes the end effector (e.g., end effector 331 of the surgical tool 231) and interfaces through one or more gears (i.e., having the gear ratio 655) that couple the grip actuator 660 to the end effector so as to controllably actuate the end effector.

Figure 7:
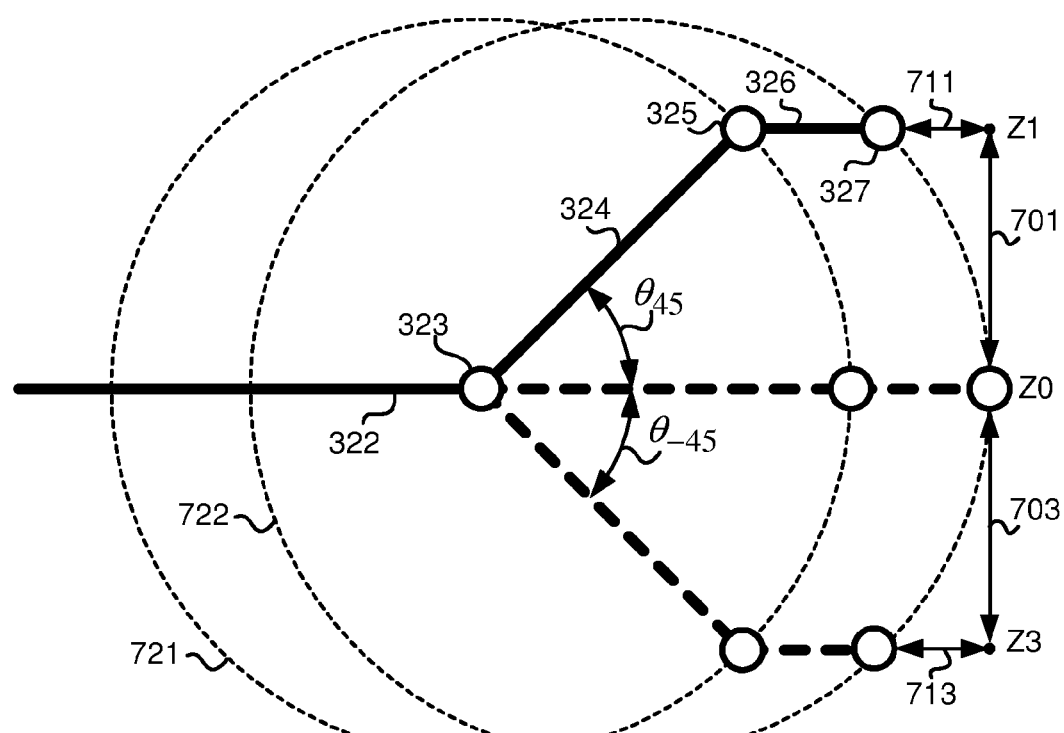
FIG. 7 illustrates a schematic kinematic diagram including a camera joggle-joint pitch assembly with indications of arc compensation for translating its movement to a translational mode movement, as used in a medical robotic system utilizing aspects of the present invention.

The group of instrument joints 600 is referred to as "translational joints" because by actuation of a combination of these joints, the instrument's wrist assembly may be positioned translationally within three-dimensional space. For example, FIG. 7 illustrates a schematic kinematic diagram of the links 322, 324, 326 and joints 323, 325 of the joggle joint pitch assembly 621 of the articulated camera 211 at three pitch angles, θ=+45, θ=0, θ=−45 degrees, with indications of corresponding arc compensation by the in/out assembly 623 so as to result in translational movement of the wrist assembly 327 in a first direction (vertical in the figure) which is orthogonal to the longitudinal axis (horizontal in the figure) of the first link 322. An indication of the longitudinal axis 401 of the first link 322 and the pitch angle 402 are shown in FIG. 4. If the camera tip 311 is in a fixed orientation relative to the wrist assembly 327 during the translational movement, then the camera tip 311 will also move in an arc corresponding to that of the wrist assembly 327 offset by a fixed length dependent upon the angle of orientation.

In this example, when the links 322, 324, 326 are fully extended outward so that the pitch angle is 0 degrees and the wrist assembly 327 is at a point Z0, no arc compensation is necessary by the in/out assembly 623 if the wrist assembly 327 is to be moved in a vertical direction along a line passing through the point Z0. On the other hand, when the second link 324 is rotated +45 degrees in pitch at the first joint 323 about a first axis which is orthogonal to the longitudinal axis 401 of the link 322, the position of the wrist assembly 327 relative to the first joint 323 has a tangential component 701. In order for the movement of the wrist assembly 327 to move in the vertical direction along the line passing through the point Z0, however, the in/out assembly 623 must move the wrist assembly 327 forward (i.e., in) to the point Z1 by a distance indicated as 711. Similarly, if the second link 324 is rotated −45 degrees in pitch at the first joint 323 about the first axis, the position of the wrist assembly 327 relative to the first joint 323 has a tangential component 703 and the in/out assembly 623 must move the wrist assembly 327 forward to a point Z3 by a distance indicated as 713 in order for the movement of the wrist assembly 327 to move along the vertical line passing through the point Z0. For other angles of pitch rotation, the second joint 325 moves along a circle 721 having a radius equal to the length of the second link 324, the wrist assembly 327 moves along a corresponding circle 722 of equal radius that is offset from the circle 721 by an amount equal to the length of the third link 326 along the longitudinal axis of the first link 322, and the arc compensation required by the in/out assembly 623 is the distance from the wrist assembly 327 to the vertical line passing through the point Z0.

The joggle joint yaw assembly 622 operates in a similar manner as the joggle joint pitch assembly 621. Except that in this case, the second link 324 is rotated at the first joint 323 about a second axis which is orthogonal to both the first axis (as used by the pitch assembly 621) and the longitudinal axis 401 of the link 322.

When the joggle joint pitch and yaw assemblies 621, 622 are actuated concurrently, such as through joggle coupling 640, the resulting movement of the wrist assembly 327 may follow a portion of a sphere (i.e., a three-dimensional version of the circle 722). In this case, if the movement of the wrist assembly 327 is to be on a plane passing through and perpendicular to the longitudinal axis of the link 322, then the compensation required by the in/out assembly 623 is the distance from the wrist assembly 327 to the plane.

Note that in the above example, it is assumed that both the joggle joint pitch and yaw assemblies 621, 622 pivot the second link 324 about the same pivot point. In practice, however, they may pivot about slightly different pivot points if the first and second joints 323, 325 are first and second joint assemblies in which each joint assembly includes a pitch joint, a yaw joint and a short link separating and coupling the pitch and yaw joints. In this case, first and second pitch joints respectively of the first and second joint assemblies 323, 325 are coupled together as part of the joggle joint pitch assembly 621, and first and second yaw joints respectively of the first and second joint assemblies 323, 325 are coupled together as part of the joggle joint yaw assembly 622. First and second short links of the first and second joint assemblies 323, 325 are referred to as being short, because they are each shorter than the first link 322, second link 324 and third link 326. The first and second short links are also constrained to be parallel to each other at all times, like the first and third links 322, 326. In addition, as may be readily appreciated in light of the geometries of the first and second joint assemblies 323, 325, rather than moving along the surface of a sphere, the wrist assembly 327 may follow a different concave virtual surface when both the joggle joint pitch and yaw assemblies 621, 622 are actuated at the same time.

Figure 8:
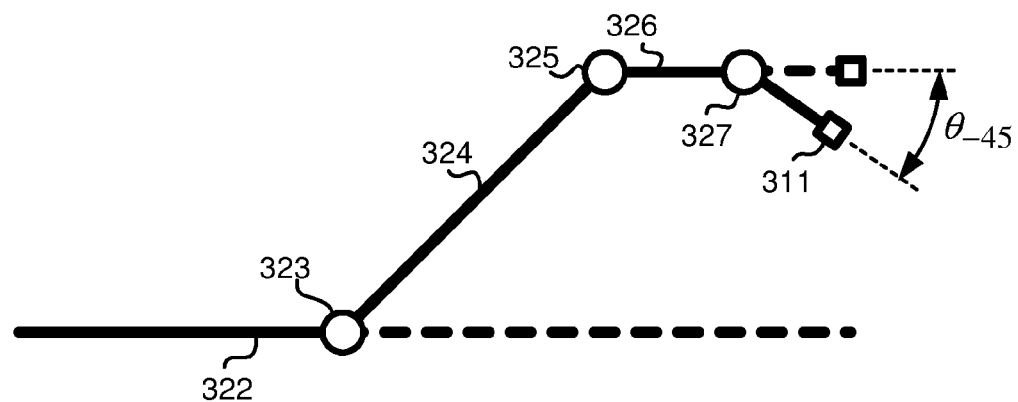
FIG. 8 illustrates a schematic kinematic diagram including a camera wrist assembly for providing orientational mode movement, as used in a medical robotic system utilizing aspects of the present invention.

The group of instrument joints 610 is referred to as "orientational joints" because by actuation of these joints, the instrument's tip may be oriented about the wrist assembly. For example, FIG. 8 illustrates a schematic kinematic diagram including the wrist assembly 327 as it pivots the camera's tip 311 about its pitch joint 632 to a −45 degrees pitch angle while the links 322, 324, 326 and joints 323, 325 of the camera instrument's joggle-joint pitch assembly 621 are controllably held in place. The wrist assembly 327 may also pivot the camera's tip 311 about its yaw joint 633 in a similar manner. When the camera's tip 311 is pivoted about both the pitch and yaw joints 632, 633 concurrently by operation of the wrist assembly 327, such as through wrist coupling 650, the resulting movement of the camera tip 311 may follow a concave virtual surface. However, if the pitch and yaw joints 632, 633 are the same joint, such as a ball joint, then the resulting movement of the camera tip 311 may follow a portion of a sphere.

Figure 9:
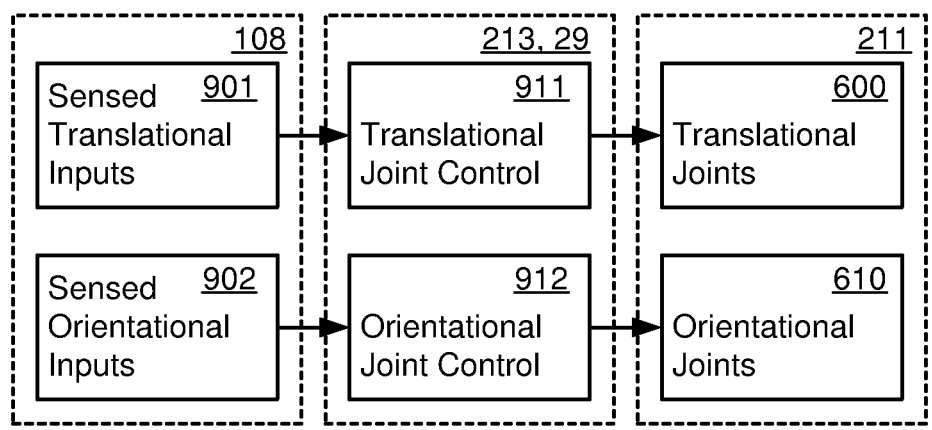
FIG. 9 illustrates a block diagram of a camera instrument control scheme using a single input device for concurrent translational and orientational mode control, as used in a medical robotic system utilizing aspects of the present invention.

FIG. 9 illustrates a block diagram in which the input device 108 is associated with and used to control positioning (i.e., translationally and orientationally) of the tip 311 of the camera instrument 211. In this example, operator manipulated movement of the three translational degrees-of-freedom of the input device 108 is sensed and used to command translational movement of the camera's wrist assembly 327 through translational joints 600 of the camera instrument 211, and operator manipulated movement of the three orientational degrees-of-freedom of the input device 108 is sensed and used to command orientational movement of the camera's tip 311 about its wrist assembly 327 through orientational joints 610 of the camera instrument 211. Because of this partitioning of the translational and orientational modes, the Surgeon generally knows which joints of the camera instrument 211 are moving (i.e., the translational joints 600 or the orientational joints 610) when manipulating the input device 108, thus providing an intuitive sense to the operator of the likelihood that the links of the camera instrument 211 will collide with the links of one of the surgical tools 231, 241 during the camera positioning process.

Figure 10:
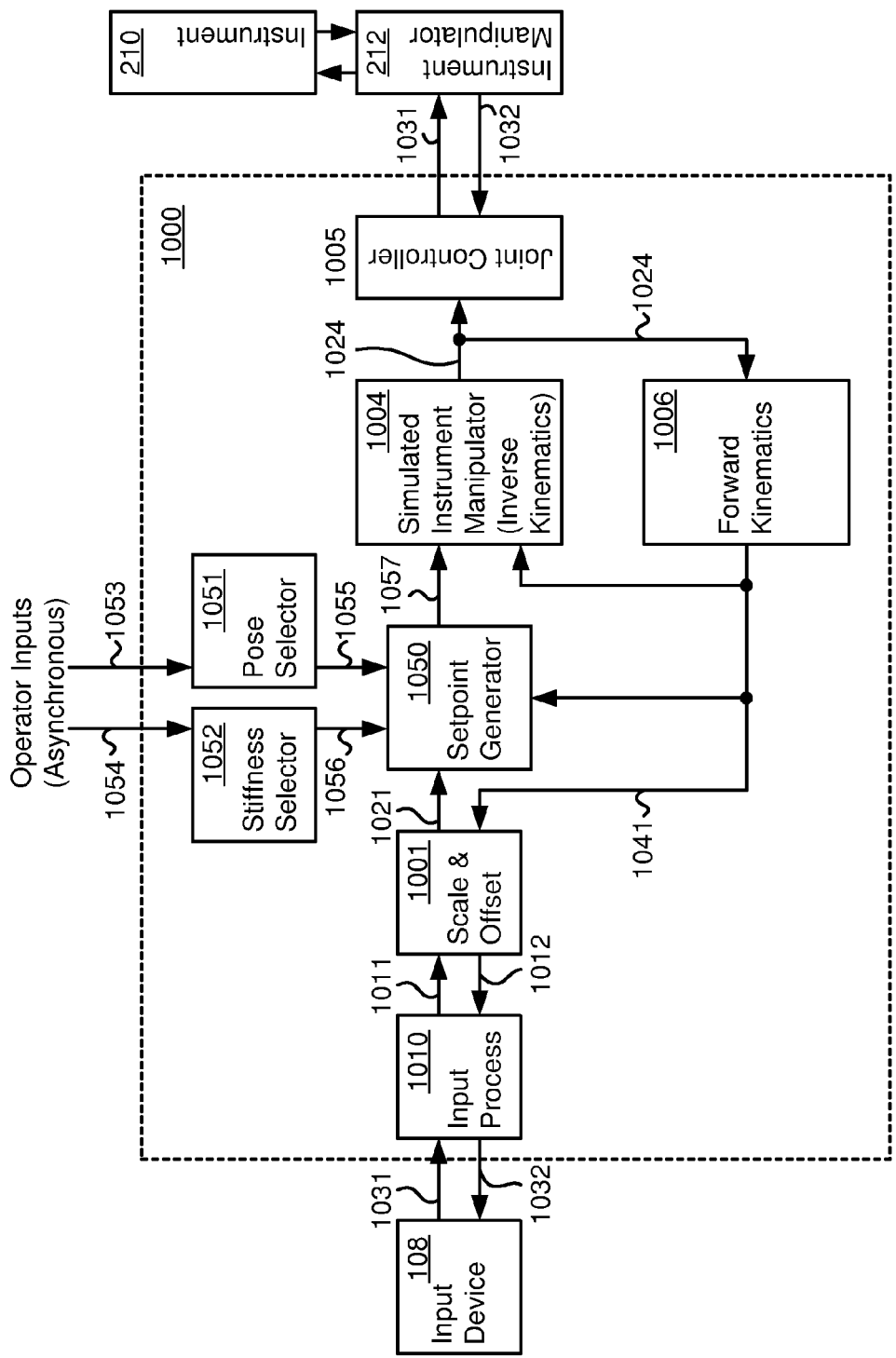
FIG. 10 illustrates a block diagram of a control system for controlling movement of an articulated camera instrument in a medical robotic system utilizing aspects of the present invention.

FIG. 10 illustrates, as an example, a block diagram of a control system 1000 for controlling positioning (i.e., both translationally and orientationally) of the camera instrument 211 in response to movement of the input device 108 when the input device 108 is selectively associated with the camera 211. Although control of the camera 211 is described, it is to be appreciated that the various blocks described herein for the control system 1000 are also applicable to the control of each of the tools 231, 241 as well as the entry guide 200. The input device 108 includes a number of links connected by joints so as to facilitate multiple degrees-of-freedom movement. For example, as the Surgeon/operator moves the input device 108 from one position to another, sensors associated with the joints of the input device 108 sense such movement at sampling intervals (appropriate for the processing speed of the processor 102 and camera control purposes) and provide digital information 1031 indicating such sampled movement in joint space to input processing blocks 1010.

Input processing block 1010 processes the information 1031 received from the joint sensors of the input device 108 to transform the information into corresponding desired positions and velocities for the camera 211 in its Cartesian space relative to a reference frame associated with the position of the Surgeon's eyes (the "eye reference frame"), by computing joint velocities from the joint position information and performing the transformation using a Jacobian matrix and eye related information using well-known transformation techniques.

Scale and offset processing block 1001 receives the processed information 1011 from the input processing block 1010 and applies scale and offset adjustments to the information so that the resulting movement of the camera instrument 211 and consequently, the image being viewed on the monitor 104 appears natural and as expected by the operator of the input device 108. The scale adjustment is useful where small movements of the camera 211 are desired relative to larger movement of the input device 108 in order to allow more precise movement of the camera instrument 211 as it views the work site. In addition, offset adjustments are applied for aligning the input device 108 with respect to the Surgeon's eyes as he or she manipulates the input device 108 to command movement of the camera instrument 211 and consequently, its captured image that is being displayed at the time on the monitor 104.

A setpoint generator block 1050 receives the commanded state vector ($\hat{X}_{DES}$) for the camera instrument 211 in the output 1021 of the scale and offset processing block 1001, a preferred pose vector ($\hat{X}_{PP}$) for the camera instrument 211 in an output 1055 of a pose selector block 1051, and weightings ($w_i$, i=1 . . . n) for the state variables of the commanded state vector ($\hat{X}_{DES}$), and calculates a setpoint vector ($\hat{X}_{SP}$) for its output 1057 by interpolating between the commanded state vector ($\hat{X}_{DES}$) and the preferred pose vector ($\hat{X}_{PP}$) using the weightings ($w_i$, i=1 . . . n) in a weighted average approach.

For example, the set point value "$f(\hat{X}_{SPi})$" for the $i^{th}$ state variable of the setpoint vector ($\hat{X}_{SP}$) may be calculated according to the following equation:

$$f(\hat{X}_{SPi}) = (1-w_i)*f(\hat{X}_{DESi}) + w_i*f(\hat{X}_{PPi}), \text{ for } 0 < w_i \le 1 \quad (1)$$

where "i" indicates the $i^{th}$ state variable, "$w_i$" is a weighting for the $i^{th}$ state variable, "$f(\hat{X}_{DESi})$" is the value for the $i^{th}$ state variable of the commanded state vector ($\hat{X}_{DES}$) for the camera instrument 211, and "$f(\hat{X}_{PPi})$" is the value for the $i^{th}$ state variable of the preferred pose vector ($\hat{X}_{PP}$) for the camera instrument 211.

State variables for the commanded state vector ($\hat{X}_{DES}$), the preferred pose vector ($\hat{X}_{PP}$), and the setpoint vector ($\hat{X}_{SP}$) preferably include translational and orientational positions and velocities for six degrees of freedom movement. Weighting coefficients can be individually selected so as to provide stiffer behavior along a specific Cartesian direction for translational movements and/or about a specified Cartesian for rotational movements. Although weightings are used for both positions and velocities of the commanded state vector ($\hat{X}_{DES}$), they are not necessarily independent of each other. In particular, the weightings for velocities may be selected, or otherwise determined in some fashion, so as to be consistent with the weightings of their respective positions (e.g., weightings for corresponding positions and velocities may be either both relatively large or both relatively small, but not one large with the other small).

Figure 11:
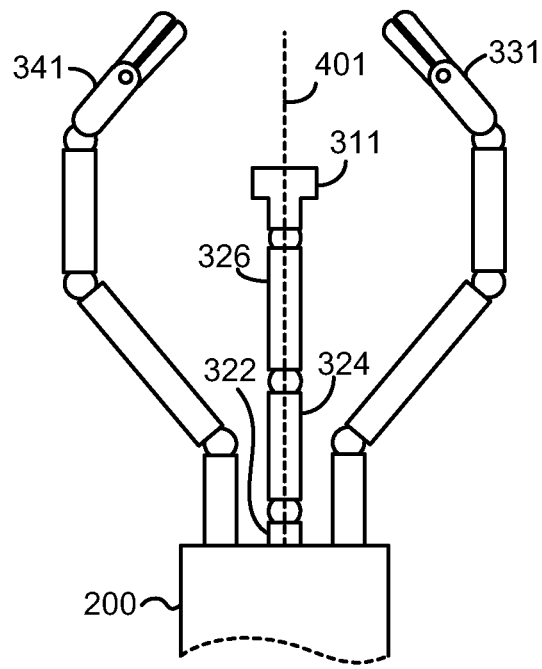
FIGS. 11-12 respectively illustrate top and right side views of a distal end of an entry guide with an articulated camera instrument in a preferred pose as used in a medical robotic system utilizing aspects of the present invention.
Figure 12:
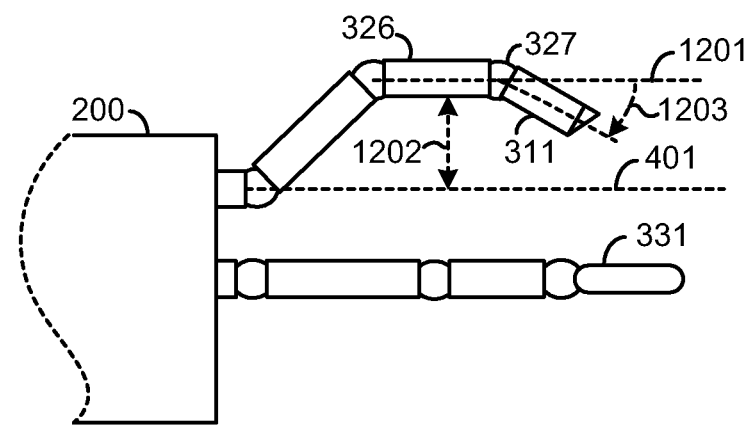

The preferred pose vector ($\hat{X}_{PP}$) provided by the camera pose selector block 1051 may be selected by the Surgeon or selected by default. FIGS. 11-12 respectively illustrate top and side views of an "optimal pose" for the camera instrument 211, which is preferably used as the default pose for the camera instrument 211. Looking downward at the optimal pose, as shown in FIG. 11, all links 322, 324, 326 of the camera instrument 211 are centered along the longitudinal axis 401 of the first link 322 so that they have maximum available range of lateral motion and provide a reference for the main insertion direction of the camera instrument 211. Further, the joggle joints 323, 325 are "joggled up", as shown in FIG. 12, so that the third link 326 is displaced a distance 1202 above the longitudinal axis 401 and the wrist assembly 327 is rotated at a negative pitch angle so that the camera tip 311 is oriented downwards at an angle 1203 so that the camera is preferably viewing the center of a workspace for the end effectors 331 and 341 of tool instruments 231 and 241, which are also extending out of the distal end of the entry guide 200 at the time. In this case, the operator is preferably allowed to freely move the camera 211 forward and backward in the input/output (I/O) direction so that the camera 211 may better view the end effectors 331, 341 as they move away from and back towards the distal end of the entry guide 200 during their use. Therefore, the setpoint generator block 1050 may use for such purpose the output 1041 of the forward kinematics block 1006 to modify the preferred pose vector ($\hat{X}_{PP}$) and guarantee that it "tracks" the operator commanded I/O movement of the camera 211.

Rather than strictly relying on the preferred pose ($\hat{X}_{PP}$) being selected by default, the Surgeon may also be provided with the capability to select the preferred pose by interacting through the pose selector block 1051. For example, the pose selector block 1051 may be implemented by the GUI 170, with a menu of instrument poses displayed on the monitor 104, one of which may be the default pose described above. The Surgeon may alternatively or additionally be provided with the capability to designate a current pose of the camera instrument 211 as the preferred pose in a number of ways such as depressing a button on the input device 108, providing a voice command understood by the voice recognition system 160, or stepping on the foot pedal 105 while the camera pose selector block 1051 is expecting an indication of such designation by the operator. The current pose is then stored in a memory as the preferred pose. As another way that the Surgeon may designate a current pose of the camera instrument 211 as the preferred pose, the Surgeon may use a computer mouse to click on a clickable icon displayed on the monitor 104 so that the current pose is stored in a memory as the preferred pose.

Figure 13:
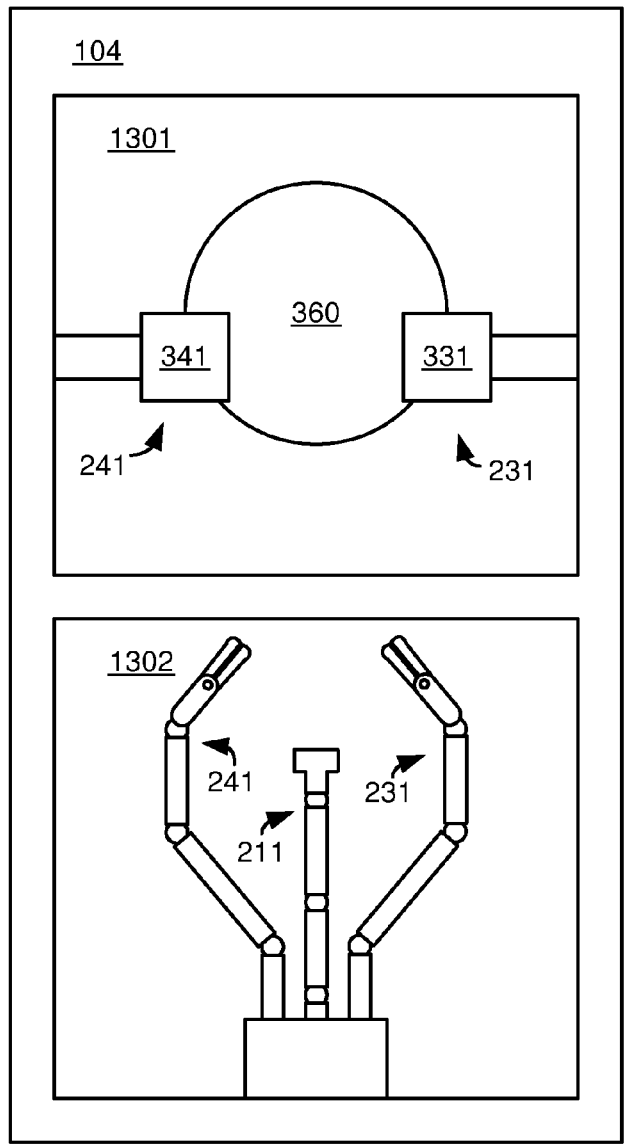
FIG. 13 illustrates an auxiliary view displayed adjacent to an image captured by the articulated camera instrument on a display screen in a medical robotic system utilizing aspects of the present invention.

To assist the Surgeon in deciding whether to designate the current pose of the camera instrument 211 as the preferred pose, an auxiliary view indicating the current configuration of the camera instrument 211 may be helpful. For example, FIG. 13 illustrates a view 1301 of a surgical site captured by the camera 211 and a corresponding auxiliary view 1302 generated by the processor 102 (using sensed position information for joints of the instrument 211 and entry guide 200) to indicate the current configuration of the camera instrument 211, as well as those of the tool instruments 231, 241, extending out of the distal end of the entry guide 200. As can be seen from the captured view 1301, very little information is provided for the positions of the non-seen joints and links of the instrument, whereas in the auxiliary view 1302, not only is information for the positions of the instrument's joints and links available, their respective positions relative to those of the other instruments 231, 241 are also available. For details on the generation of such computer generated auxiliary views, see, e.g., U.S. Pub. Applic. No. 2009/0326553 "Medical Robotic System Providing an Auxiliary View of Articulatable Instruments Extending out of a Distal End of an Entry Guide," which is incorporated herein by this reference. Although FIG. 13 shows both the captured image 1301 and the auxiliary view 1302 being displayed on the monitor 104, the auxiliary view 1302 may be viewed instead on a separate auxiliary display (not shown).

Figure 14:
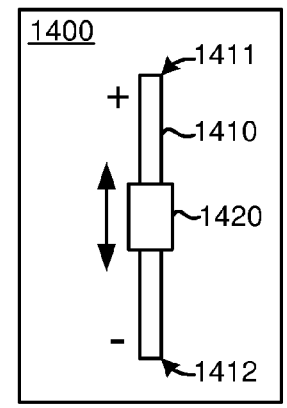
FIG. 14 illustrates a user interactive, graphical sliding control for adjusting a weighting used to calculate a setpoint for controlling movement of an articulated instrument in a medical robotic system utilizing aspects of the present invention.

In addition to specifying the preferred pose ($\hat{X}_{PP}$) through the camera pose selector block 1051, the Surgeon may also specify the weighting for each of the state variables used for calculating the setpoint in equation (1) using the stiffness selector block 1052. For example, the value for each weighting may be selected by the Surgeon interacting through the stiffness selector block 1052 with a corresponding graphical indicator displayed on the monitor 104, such as the user interactive, graphical slide control 1400 shown in FIG. 14. Using the graphical slide control 1400, any value for a weighting "$w_i$" between a maximum of "1" and a minimum of "0" may be selected by the Surgeon by placing a cursor on a graphical slide 1420 and causing the graphical slide 1420 to move up towards the top limit 1411 or down towards the bottom limit 1412 of a graphical scale 1410 while depressing a button on a mouse controlling movement of the cursor. Thus, separate weights may be defined by the Surgeon for each state variable so as to suit the Surgeon's personal preferences. A user selectable icon may also be provided for convenience on the monitor 104 by the stiffness selector block 1052, which when selected by the Surgeon sets all weights to "0" so as to allow the Surgeon to disable the centering behavior. Another user selectable icon may also be provided for convenience on the monitor 104 which when selected by the Surgeon sets all weights to "1" so as to effectively lock the camera instrument 211 in the preferred pose ($\hat{X}_{PP}$). It is important to note, however, that as long as the selected weighting is less than "1", the Surgeon is able to over-power any restoring force felt at the input device 108 as a result of such weighting and drive the camera to a desired position away from the preferred pose. Thus, the Surgeon still has full control over the motion of the camera instrument 211 in such case.

A simulated camera manipulator block 1004 transforms the setpoint vector ($\hat{X}_{SP}$) received on the output 1057 of the setpoint generator 1050 from the Cartesian space of the camera instrument 211 to its joint space using its inverse kinematics while avoiding singularities in its operation, limiting the commanded joint positions and velocities to avoid physical limitations or other constraints such as avoiding harmful contact with tissue or other parts of the Patient, and applying virtual constraints that may be defined to improve the performance of a medical procedure being performed at the time by the Surgeon using the medical robotic system 100.

The output 1024 of the simulated camera manipulator block 1004 is provided to a joint controller block 1005 and a forward kinematics block 1006. The joint controller block 1005 includes a joint control system for each controlled joint (or operatively coupled joints such as "joggle joints") of the camera instrument 211. The output 1024 of the simulated camera manipulator block 1004 provides the commanded value for each joint of the camera instrument 211. For feedback control purposes, sensors associated with each of the controlled joints of the camera instrument 211 provide sensor data 1032 back to the joint controller block 1005 indicating the current position and/or velocity of each joint of the camera instrument 211. The sensors may sense this joint information either directly (e.g., from the joint on the camera instrument 211) or indirectly (e.g., from the actuator in the camera manipulator 212 driving the joint). Each joint control system in the joint controller 1005 then generates torque commands for its respective actuator in the camera manipulator 212 so as to drive the difference between the commanded and sensed joint values to zero in a conventional feedback control system manner.

The forward kinematics block 1006 transforms the output 1024 of the simulated camera manipulator block 1004 from joint space back to Cartesian space relative to the eye reference frame using the forward kinematics of the camera instrument 211. The output 1041 of the forward kinematics block 1006 is provided to the scale and offset processing block 1001 as well as the simulated camera manipulator block 1004 for its internal computational purposes and the setpoint generator block 1050 for modifying the preferred pose vector ($\hat{X}_{PP}$) and/or weightings ($w_i$, i=1 ... n) as previously described or otherwise as appropriate.

The scale and offset processing block 1001 performs inverse scale and offset functions on the output 1041 of the forward kinematics block 1006 before passing its output 1012 to the input processing block 1010 where an error value is calculated between its output 1011 and input 1012. If no limitation or other constraint had been imposed on the input 1021 to the simulated camera manipulator block 1004, then the calculated error value would be zero. On the other hand, if a limitation or constraint had been imposed, then the error value is not zero and it is converted to a torque command 1032 that drives actuators in the input device 108 to provide force feedback felt by the hands of the Surgeon. Thus, the Surgeon becomes aware that a limitation or constraint is being imposed by the force that he or she feels resisting his or her movement of the input device 108 in that direction.

In the present case, since the setpoint generator 1050 commands the simulated camera manipulator block 1004 to be driven to the setpoint vector ($\hat{X}_{SP}$) rather than the commanded state vector ($\hat{X}_{DES}$), an error value is calculated by the input processing block 1010 between its output 1011 and input 1012. As a result, the Surgeon perceives a spring-type force feedback on the input device 108 whenever the Surgeon is commanding the camera instrument 211 away from the preferred pose ($\hat{X}_{PP}$). The force feedback in this case is actually a vector of forces and torques, each applied in a different degree-of-freedom of the input device 108. In particular, since there is a direct relationship between translational and orientational movement of the input device and the commanded translational and orientational movement of the camera 211 in the system 100, as previously described, the weightings ($w_i$, i=1 . . . n) applied by the setpoint generator 1050 also serve to determine the magnitudes of the force feedback in each of the translational and orientational directions in the form of forces and torques felt by the Surgeon on the input device 108. Thus, heavier weighted state variables that refer to translational movement of the input device 108 and camera 211 result in higher force feedback gains felt on the input device 108 as resisting translational movement away from the preferred pose ($\hat{X}_{PP}$) and heavier weighted state variables that refer to orientational movement of the input device 108 and camera 211 result in higher torque feedback gains felt on the input device 108 as resisting orientational movement away from the preferred pose ($\hat{X}_{PP}$) To ensure that excessive friction in the input device 108 does not "overshadow" the "nudging" force felt on the input device 108, conventional friction and stiction compensation techniques may be used.

In addition, a non-linear characteristic may be used for the restoring force and torque, in order to modulate the stiffness as a function of the distance from the preferred pose and possibly of the velocity. For example, a deadband characteristic may be provided so that unconstrained operator commanded motion is allowed "nearby" the preferred pose ($\hat{X}_{PP}$) (i.e., no restoring force/toque feedback is applied within a threshold distance from the preferred pose) and the restoring force/torque is only felt beyond the threshold distance. At the threshold distance, the restoring force/torque feedback may or may not be applied as determined by default or operator selection.

Although the preferred pose mechanism described in reference to FIG. 10 above may be particularly useful in controlling movement of a bundled camera such as the camera instrument 211, it may also be useful in controlling movement of a bundled tool such as the tool instruments 231, 241 and/or controlling movement of an entry guide in which the bundled instruments are guided to a surgical site within a patient. For example, a preferred pose for one of the tool instruments 231, 241 may be a pose wherein its links are all aligned (i.e., the longitudinal axes of the links are aligned so that they coincide with each other). This pose would be useful during the retraction of the tool instrument back into the entry guide 200, for example. A preferred pose for the entry guide 200, on the other hand, may be one in which it points towards a target site in the patient or one in which a wide range of motion is provided for each of the tool instruments extending out of its distal end.

Although the various aspects of the present invention have been described with respect to a preferred embodiment, it will be understood that the invention is entitled to full protection within the full scope of the appended claims.

What is claimed is:

1. A medical system comprising:
   an entry guide;
   a plurality of articulated instruments extending through the entry guide;
   an input device associated with an associated articulated instrument of the plurality of articulated instruments; and
   a controller configured to command manipulation of the associated articulated instrument according to a weighted average, using non-zero weights, of a commanded pose of the associated articulated instrument and a preferred pose of the associated articulated instrument, wherein the commanded pose of the associated articulated instrument is commanded by manipulation of the input device by an operator.

2. The medical system according to claim 1, wherein the controller is configured to command sensory feedback to the operator of the input device so as to indicate a difference between the commanded pose and the preferred pose of the associated articulated instrument.

3. The medical system according to claim 2, wherein the sensory feedback comprises haptic feedback to the input device, and wherein the haptic feedback provides a perception to the operator of a spring-type force feedback on the input device whenever the operator is commanding the associated articulated instrument away from the preferred pose.

4. The medical system according to claim 3, wherein the haptic feedback comprises a restoring sensation applied to the input device that urges the operator to manipulate the input device in one or more directions to command the associated articulated instrument to the preferred pose.

5. The medical system according to claim 4, wherein the restoring sensation comprises a restoring force exerted against each translational movement of the input device commanding the associated articulated instrument away from the preferred pose and a restoring torque exerted against rotational movement of the input device commanding the associated articulated instrument away from the preferred pose.

6. The medical system according to claim 5, wherein the controller is configured to command at least one of the restoring force and torque according to a spring function.

7. The medical system according to claim 6, wherein the spring function is characterized by a dead zone.

8. The medical system according to claim 6, wherein the spring function is characterized by friction compensation.

9. The medical system according to claim 6, wherein the spring function is non-linear.

10. The medical system according to claim 1, wherein the associated articulated instrument is an articulated camera instrument and the preferred pose of the associated articulated instrument corresponds to an optimal pose of the articulated camera instrument for viewing at least one other of the plurality of articulated instruments by a camera of the articulated camera instrument.

11. The medical system according to claim 10, wherein the optimal pose maximizes viewability of the others of the plurality of articulated instruments within a field of view of the camera.

12. The medical system according to claim 10, wherein the optimal pose is characterized by the camera being extended directly above a longitudinal axis of a proximal link of the articulated camera instrument and oriented downwards towards the longitudinal axis at an angle sufficient to capture end effectors of the others of the plurality of articulated instruments in a field of view of the camera.

13. The medical system according to claim 1, further comprising a pose selector, wherein the preferred pose of the associated articulated instrument is selected by the operator interacting with the pose selector.

14. The medical system according to claim 13, wherein the controller is configured to store information of the pose selected by the operator in a memory by storing information of a current pose of the associated articulated instrument upon receiving an indication to do so by the operator interacting with the pose selector.

15. The medical system according to claim 13, wherein the controller is configured to receive information of the pose selected by the operator by receiving an operator selection of one of a plurality of programmed poses for the associated articulated instrument, and wherein the operator selection is indicated by the operator interacting with the pose selector.

16. The medical system according to claim 1, wherein the weighted average is calculated by an interpolation of the commanded pose and the preferred pose of the associated articulated instrument.

17. The medical system according to claim 1, wherein the commanded pose includes a Cartesian position variable and a Cartesian orientation variable, and the weighted average is calculated by applying weights to the Cartesian position and Cartesian orientation variables.

18. The medical system according to claim 17, wherein at least one of the Cartesian position and Cartesian orientation variables has a corresponding programmable weight applied to it.

19. The medical system according to claim 18, wherein the controller is configured to receive information of the corresponding programmable weight from a graphical user interface operated by the operator.

20. The medical system according to claim 18, wherein the controller generates the haptic feedback according to a plurality of spring functions, wherein a first one of the plurality of spring functions applies to a position variable of the position and orientation variables, and wherein a second one of the plurality of spring functions applies to an orientation variable of the position and orientation variables.

21. The medical system according to claim 17, wherein the commanded pose includes a Cartesian translational variable and a Cartesian angular velocity variable, and the weighted average is calculated by applying weights to the Cartesian translational and Cartesian angular velocity variables.

22. The medical system according to claim 21, wherein each of the Cartesian translational and Cartesian angular velocity variables has a corresponding programmable weight applied to it.

23. The medical system according to claim 22, wherein the controller is configured to receive information of the corresponding programmable weight from a graphical user interface operated by the operator.

24. The medical system according to claim 1, wherein the associated articulated instrument is an articulated tool instrument.

25. The medical system according to claim 24, wherein the preferred pose of the associated articulated instrument is a pose of the articulated tool instrument wherein all links of the articulated tool instrument are aligned.

26. The medical system according to claim 24, wherein the preferred pose of the associated articulated instrument corresponds to a pose selected by the operator.

27. The medical system according to claim 10, wherein the optimal pose minimizes a likelihood of collision between the articulated camera instrument and the others of the plurality of articulated instruments.

28. A medical system comprising:
an entry guide;
a plurality of articulated instruments extending through the entry guide;
an input device associated with the entry guide; and
a controller configured to command manipulation of the entry guide according to a weighted average, using non-zero weights, of a commanded pose of the entry guide and a preferred pose of the entry guide, wherein the commanded pose of the entry guide is commanded by manipulation of the input device by an operator.

29. The medical system according to claim 28, wherein the controller is configured to command sensory feedback to the operator of the input device so as to indicate a difference between the commanded pose and the preferred pose of the entry guide.

30. The medical system according to claim 29, wherein the preferred pose of the entry guide directs a distal end of the entry guide towards a target area.

31. The medical system according to claim 28, wherein the preferred pose of the entry guide corresponds to a pose selected by the operator.

32. A method implemented in a medical system having an entry guide, a plurality of articulated instruments extending through the entry guide, and an input device associated with an associated articulated instrument of the plurality of articulated instruments, the method comprising:
manipulating the associated articulated instrument towards a commanded pose that is commanded by manipulation of the input device by an operator and that is biased towards a preferred pose of the associated articulated instrument according to a weighted average, using non-zero weights, of the commanded pose of the associated articulated instrument and the preferred pose of the associated articulated instrument.

33. The method according to claim 32, further comprising:
providing a spring-type force feedback on the input device whenever the operator is commanding the associated articulated instrument from the preferred pose of the associated articulated instrument, wherein the providing of the spring-type force feedback comprises applying a restoring sensation to the input device that urges the operator to manipulate the input device in one or more directions to command the associated articulated instrument to the preferred pose.

34. The method according to claim 33, wherein the applying of the restoring sensation comprises:
exerting a restoring force against each translational movement of the input device commanding the associated articulated instrument away from the preferred pose; and
exerting a restoring torque against each rotational movement of the input device commanding the associated articulated instrument away from the preferred pose.

35. The method according to claim 34, further comprising generating at least one of the restoring force and torque according to a spring function.

36. The method according to claim 35, wherein the spring function is characterized by a dead zone.

37. The method according to claim 35, wherein the spring function is characterized by friction compensation.

38. The method according to claim 35, wherein the spring function is non-linear.

39. The method according to claim 32, wherein the associated articulated instrument is an articulated camera instrument and the preferred pose of the associated articulated instrument corresponds to an optimal pose of the articulated camera instrument for viewing at least one other of the plurality of articulated instruments by a camera of the articulated camera instrument.

40. The method according to claim 39, wherein the optimal pose maximizes viewability of the others of the plurality of articulated instruments within a field of view of the camera.

41. The method according to claim 39, wherein the optimal pose is characterized by the camera being extended directly above a longitudinal axis of a proximal link of the articulated camera instrument and oriented downwards towards the longitudinal axis at an angle sufficient to capture end effectors of the others of the plurality of articulated instruments in a field of view of the camera.

42. The method according to claim 32, wherein the associated articulated instrument is an articulated camera instrument and the preferred pose of the associated articulated instrument corresponds to a pose selected by the operator.

43. The method according to claim 42, further comprising storing information of the pose selected by the operator in a memory by storing information of a current pose of the associated articulated instrument upon receiving an indication to do so from the operator.

44. The method according to claim 42, further comprising receiving information of the pose selected by the operator by receiving an operator selection of one of a plurality of programmed poses for the associated articulated instrument.

45. The method according to claim 32, further comprising calculating the weighted average by an interpolation of the commanded pose and the preferred pose of the associated articulated instrument.

46. The method according to claim 32, wherein the commanded pose includes a Cartesian position variable and a Cartesian orientation variable, and the weighted average is calculated by applying weights to the Cartesian position and Cartesian orientation variables.

47. The method according to claim 46, wherein each of the Cartesian position and Cartesian orientation variables has a corresponding programmable weight applied to it.

48. The method according to claim 47, further comprising receiving information of the corresponding programmable weight from a graphical user interface operated by the operator.

49. The method according to claim 47, further comprising generating the haptic feedback according to a plurality of spring functions wherein a first one of the plurality of spring functions applies to a position variable of the position and orientation variables, and wherein a second one of the plurality of spring functions applies to an orientation variable of the position and orientation variables.

50. The method according to claim 46, wherein the commanded pose includes a Cartesian translational variable and a Cartesian angular velocity variable, and the weighted average is calculated by applying weights to the Cartesian translational and Cartesian angular velocity variables.

51. The method according to claim 50, wherein each of the Cartesian translational and Cartesian angular velocity variables has a corresponding programmable weight applied to it.

52. The method according to claim 51, further comprising receiving information of the corresponding programmable weight from a graphical user interface operated by the operator.

53. The method according to claim 32, wherein the associated articulated instrument is an articulated tool instrument.

54. The method according to claim 53, wherein the preferred pose of the associated articulated instrument is a pose of the articulated tool instrument wherein all links of the articulated tool instrument are aligned.

55. The method according to claim 53, wherein the preferred pose of the associated articulated instrument corresponds to a pose of the articulated tool instrument that has been selected by the operator.

56. The medical method according to claim 39, wherein the optimal pose minimizes a likelihood of collision between the articulated camera instrument and the others of the plurality of articulated instruments.

57. A method implemented in a medical system having an entry guide, a plurality of articulated instruments extending through the entry guide, and an input device associated with the entry guide, the method comprising:
manipulating the entry guide towards a commanded pose that is commanded by manipulation of the input device by an operator and that is biased towards a preferred pose of the entry guide according to a weighted average, using non-zero weights, of the commanded pose of the entry guide and the preferred pose of the entry guide.

58. The method according to claim 57, wherein the preferred pose of the entry guide directs a distal end of the entry guide towards a target area.

59. The method according to claim 57, wherein the preferred pose of the entry guide corresponds to a pose selected by the operator.

60. The method according to claim 57, further comprising: providing a spring-type force feedback on the input device whenever the operator is commanding the entry guide away from the preferred pose of the entry guide.

* * * * *